(12) United States Patent
Morinaga et al.

(10) Patent No.: US 6,935,101 B2
(45) Date of Patent: Aug. 30, 2005

(54) HEATING CONTROL SYSTEM FOR GAS SENSOR OF ENGINE

(75) Inventors: Syujiro Morinaga, Takahama (JP); Kouichi Shimizu, Handa (JP)

(73) Assignee: Denso Corporation (JP)

( * ) Notice: Subject to any disclaimer, the term of this patent is extended or adjusted under 35 U.S.C. 154(b) by 0 days.

(21) Appl. No.: 10/631,855

(22) Filed: Aug. 1, 2003

(65) Prior Publication Data

US 2004/0026408 A1 Feb. 12, 2004

(30) Foreign Application Priority Data

Aug. 9, 2002 (JP) ........................................ 2002-232851

(51) Int. Cl.$^7$ ................................................. F01N 3/00
(52) U.S. Cl. ........................ 60/284; 60/276; 73/23.32; 123/685; 123/697; 219/494; 219/492
(58) Field of Search ........................ 60/274, 276, 284; 123/685, 697, 672, 676; 73/23.31, 23.32; 701/102, 103, 109; 219/202, 492, 494, 497

(56) References Cited

U.S. PATENT DOCUMENTS

| | | | |
|---|---|---|---|
| 4,765,298 A | * | 8/1988 | Kojima et al. ............... 123/697 |
| 5,353,774 A | * | 10/1994 | Furuya ........................ 123/685 |
| 5,518,600 A | * | 5/1996 | Uchinami .................... 204/401 |
| 5,616,835 A | * | 4/1997 | Schnaibel et al. .......... 73/117.2 |
| 5,852,228 A | | 12/1998 | Yamashita et al. |
| 6,304,813 B1 | * | 10/2001 | Ikeda et al. .................. 701/109 |
| 6,476,364 B1 | * | 11/2002 | Shimamura et al. ........ 219/494 |
| 6,723,965 B2 | * | 4/2004 | Ohkuma et al. ............ 219/497 |
| 6,812,436 B2 | * | 11/2004 | Nomura et al. ............. 219/497 |

FOREIGN PATENT DOCUMENTS

| | | |
|---|---|---|
| JP | 2000-74873 | 3/2000 |
| JP | 2002-156354 | 5/2002 |

* cited by examiner

Primary Examiner—Tu M. Nguyen
(74) Attorney, Agent, or Firm—Nixon & Vanderhye PC

(57) ABSTRACT

An electronic control unit of an internal combustion engine performs preheat energization control before activation energization control. In the activation energization control, a gas sensor is energized with electric power capable of heating the gas sensor to activation temperature. In the preheat energization control, the gas sensor is energized with low electric power, which is not enough to heat the gas sensor to the activation temperature. Thus, while there is a possibility that water adheres to a sensor main body of the gas sensor, the sensor main body is prevented from being heated to high temperature. Meanwhile, even if water droplets exist in the sensor main body of the gas sensor, the water is vaporized gradually, while preventing the bumping of the water.

10 Claims, 5 Drawing Sheets

| Touttemp °C | tht (sec) | | | | | | |
|---|---|---|---|---|---|---|---|
| | 0 | 5 | 10 | 15 | 30 | 50 | 100 |
| -40 | 10 | 10 | 10 | 10 | 10 | 10 | 100 |
| -30 | 30 | 30 | 30 | 30 | 30 | 30 | 100 |
| -20 | 30 | 30 | 100 | 100 | 100 | 100 | 100 |
| -10 | 30 | 30 | 100 | 100 | 100 | 100 | 100 |
| 0 | 100 | 100 | 100 | 100 | 100 | 100 | 100 |
| 20 | 100 | 100 | 100 | 100 | 100 | 100 | 100 |
| 50 | 100 | 100 | 100 | 100 | 100 | 100 | 100 |
| 80 | 100 | 100 | 100 | 100 | 100 | 100 | 100 |

HEATING CONTROL SYSTEM FOR GAS SENSOR OF ENGINE

CROSS REFERENCE TO RELATED APPLICATION

This application is based on and incorporates herein by reference Japanese Patent Application No. 2002-232851 filed on Aug. 9, 2002.

BACKGROUND OF THE INVENTION

1. Field of the Invention

The present invention relates to a heating control system for a gas sensor of an internal combustion engine, in particular, to a method of preventing damage to the gas sensor.

2. Description of Related Art

An internal combustion engine has a gas sensor in an exhaust pipe for detecting concentration of gas such as oxygen included in exhaust gas discharged from an engine main body. Detection signals provided by the gas sensor are used in control of various parts of the engine main body.

A publicly used gas sensor is constituted with a base substrate made of an oxygen-ion conductive solid electrolyte such as zirconia. Such a gas sensor utilizes an attribute of the oxygen-ion to diffuse into the solid electrolyte. In the gas sensor, a cavity is formed so that the oxygen can pass between an outside of the substrate, where detected gas exists, and an inside of the substrate. For instance, the cavity is formed so that the cavity communicates with the outside of the substrate through a diffusion layer having diffusion resistance. The oxygen in the cavity is pumped by a pump cell, whose electrodes are formed on both sides of the solid electrolyte constituting a part of a peripheral wall of the cavity. Thus, limiting current flows between the electrodes. Concentration of the gas is measured based on the value of the limiting current.

In such a gas sensor, the solid electrolyte needs to be heated to activation temperature to enable the detection of the gas concentration. Therefore, the gas sensor is integrated with a heater for heating the solid electrolyte to the activation temperature. After the engine is started, a heating control system of the gas sensor performs activation energization control for energizing the heater with driving power capable of heating the gas sensor to the activation temperature. Normally, the maximum driving power is outputted in order to immediately monitor the exhaust gas passing through the exhaust pipe.

However, zirconia or the like, which is commonly used as a material of the solid electrolyte of the gas sensor, has a fragile nature. Since the gas sensor is disposed in the exhaust pipe through which the exhaust gas including a large amount of moisture passes, the gas sensor may be damaged due to rapid displacement of heat from the gas sensor to water if water droplets contact the gas sensor in a state in which the water droplets can receive the heat from the gas sensor.

However, improvement of durability of the gas sensor by improving the structure of the gas sensor has a limitation.

SUMMARY OF THE INVENTION

It is therefore an object of the present invention to provide a control system for a gas sensor of an internal combustion engine capable of preventing damage to the gas sensor.

According to an aspect of the present invention, a heating control system, which controls energization to a heater of a gas sensor disposed in an exhaust pipe of an internal combustion engine, includes exhaust pipe water determining means and activation energization controlling means. The exhaust pipe water determining means determines whether water droplets exist in the exhaust pipe when the engine is started. The activation energization controlling means performs activation energization control for energizing the gas sensor with electric power capable of heating the gas sensor to activation temperature when a predetermined waiting period passes since the engine is started if the exhaust pipe water determining means determines affirmatively.

While there is a possibility that the water droplets exist in the exhaust pipe, heating performance of the gas sensor is relatively low. In such a case, water droplets do not receive heat rapidly even if the water droplets adhere to the surface of the gas sensor. As a result, damage to the gas sensor can be prevented.

Furthermore, if there is no droplet in the exhaust pipe, the gas sensor is heated immediately. Therefore, delay in starting timing of the activation energization control can be minimized. Thus, requirement for quick increase in the gas sensor temperature can be met.

According to another aspect of the present invention, a heating control system, which controls energization to a heater of a gas sensor disposed in an exhaust pipe of an internal combustion engine, has preheat energization controlling means. The preheat energization controlling means performs preheat energization control before activation energization control for energizing the gas sensor with electric power capable of heating the gas sensor to the activation temperature. The preheat energization controlling means energizes the gas sensor with lower electric power in the preheat energization control than in the activation energization control so that water droplets in the gas sensor vaporize gradually. Thus, even if the water droplets exist in the gas sensor, the water droplets are vaporized gradually, preventing bumping of the water droplets. Therefore, the bumping of the water droplets is prevented when the activation energization control is performed. In addition, the temperature of the gas sensor has been heated to some extent by the time when the water droplets in the gas sensor vaporize sufficiently and the activation energization control is started. Therefore, the gas sensor can be heated to the activation temperature quickly. If the water droplets penetrate the diffusion layer and the like into the gas sensor from the outside during the engine is stopped and if the gas sensor is heated with the electric power capable of heating the gas sensor to the activation temperature, the heat of the gas sensor may produce bumping of the water, and the gas sensor may be damaged.

BRIEF DESCRIPTION OF THE DRAWINGS

Features and advantages of embodiments will be appreciated, as well as methods of operation and the function of the related parts, from a study of, the following detailed description, the appended claims, and the drawings, all of which form a part of this application. In the drawings:

DETAILED DESCRIPTION OF THE REFERRED EMBODIMENTS (First Embodiment)

Figure 1:
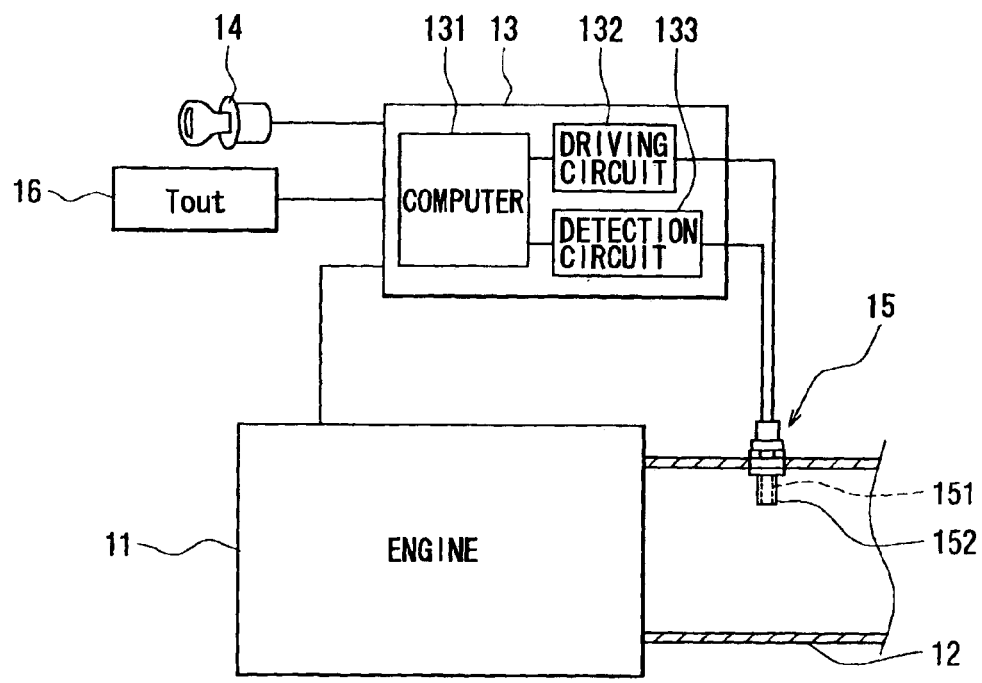
FIG. 1 is a schematic diagram showing a heating control system for a gas sensor of an internal combustion engine according to a first embodiment of the present invention.

Referring to FIG. 1, an internal combustion engine having a heating control system of a gas sensor according to the first embodiment is illustrated. The first embodiment is applied to an automobile, for instance. An engine main body 11 of the internal combustion engine has a common structure. The engine main body 11 generates motive energy by combusting fuel and discharges exhaust gas to an exhaust pipe 12.

Various parts of the engine main body 11 are controlled by an electronic control unit (ECU) 13. The ECU 13 has a basic structure used in the common internal combustion engine. The ECU 13 starts the engine main body 11 if an ignition key 14 is switched on and controls torque or rotation speed based on information such as a throttle opening degree.

Various sensors provide information on operating conditions, which is used in the control performed by the ECU 13. As one of the sensors outputting detection signals to the ECU 13, an air fuel ratio sensor unit (A/F sensor unit) 15 is disposed in the exhaust pipe 12 for detecting an air fuel ratio in combustion chambers of the engine main body 11 based on oxygen concentration in the exhaust gas. The A/F sensor unit 15 is mounted to penetrate the exhaust pipe 12. An A/F sensor 151 as a sensor main body is placed inside the exhaust pipe 12 as shown in FIG. 1. The A/F sensor 151 is covered by a covering member 152, which is formed in the shape of a cylinder having a bottom surface. The exhaust gas as detected gas reaches a surface of the A/F sensor 151 through communication holes of the covering member 152.

Figure 2:
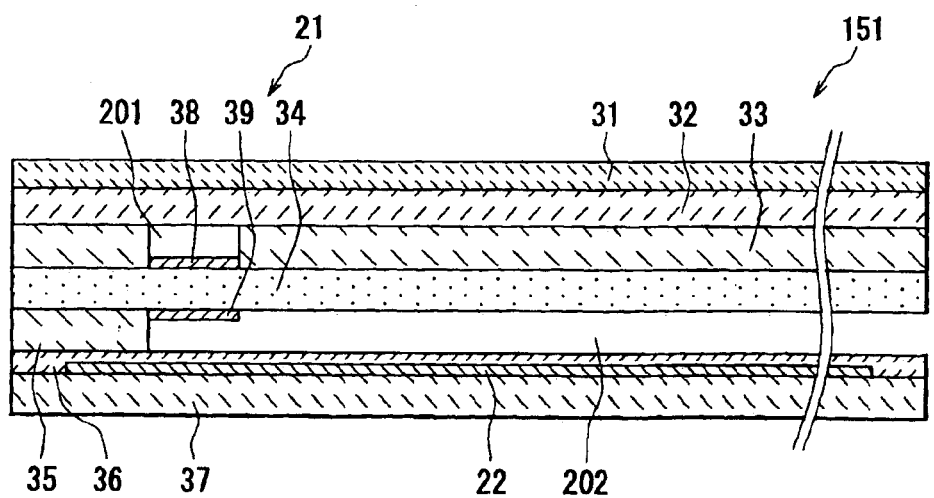
FIG. 2 is a cross-sectional view showing a substantial part of the gas sensor according to the first embodiment.

The A/F sensor 151 is common limiting current type, for instance. The A/F sensor 151 has a layered structure with a plurality of layers in which solid electrolyte such as zirconia or alumina in the shape of sheet is layered on an elongate substrate 37 as shown in FIG. 2. The solid electrolyte has the same shape as the substrate 37. The layered structure includes a trap layer 31 for eliminating extraneous matters, a diffusion layer 32 through which the gas can pass at a certain diffusion resistance, a spacer 33, a solid electrolyte layer 34 and a spacer 35, which are layered in that order from the top of the layered structure shown in FIG. 2. The upper spacer 33 is formed with a groove penetrating the spacer 33 in a direction perpendicular to the layers. Thus, a cavity 201 is formed between the diffusion layer 32 and the solid electrolyte layer 34. Electrodes 38, 39 are formed on both sides of the solid electrolyte layer 34 at the place where the cavity 201 is formed. Thus, a pump cell 21 is formed with the solid electrolyte layer 34 and the electrodes 38, 39.

An insulation layer 36 is disposed under the lower spacer 35, and the substructure 37 is disposed under the insulation layer 36, or at the bottom. The spacer 35 is formed with a notch extending in parallel with the layers from the place where the electrodes 38, 39 are formed. The notch of the spacer 35 provides an atmosphere passage 202, which communicates with the atmosphere outside the exhaust pipe 12.

The substrate 37 has a heater 22, which is a conductive thin layer formed on the surface of the substrate 37 in pattern formation. The heater 22 heats the entire sensor main body 151 under energization control performed by a driving circuit 132 of the ECU 13. The driving circuit 132 changes driving current applied to the heater 22 by regulating a duty ratio (a ratio of an on-duty state).

If a detection circuit 133 of the ECU 13 applies a predetermined voltage between the electrodes 38, 39, limiting current corresponding to the oxygen concentration flows between the electrodes 38, 39. The oxygen concentration, or the air fuel ratio, can be measured by measuring the limiting current with the detection circuit 133.

The ECU 13 also receives detection signals from sensors mounted on the common engine such as an ambient temperature sensor 16, cooling water temperature sensor and the like.

The ECU 13 has a general structure constituted centering on a microcomputer 131. The ECU 13 has various peripheral circuits such as driving circuits and input-output circuits capable of communicating with the microcomputer 131 in one-way or two-way communication. The detection circuit 133, which is one of the peripheral circuits, is connected with the electrodes 38, 39 of the pump cell 21 of the A/F sensor 151. The driving circuit 132, which is one of the peripheral circuits, is connected with the heater 22 of the A/F sensor 151. The microcomputer 131 is constituted with a CPU for performing calculation, RAM as a working storage, ROM for storing control programs or various data, backup RAM and the like.

Figure 3:
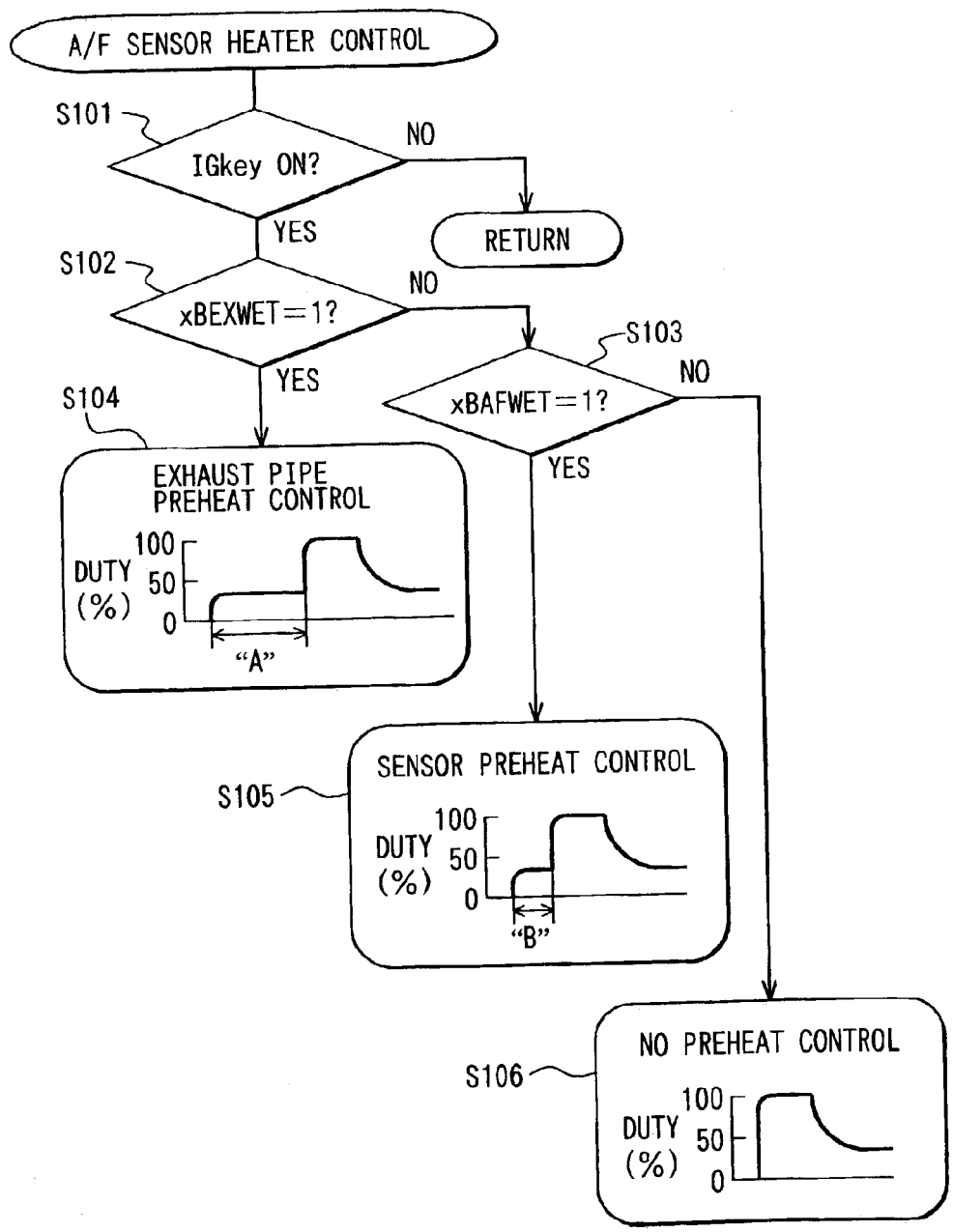
FIG. 3 is a first flowchart executed by an electronic control unit of the engine according to the first embodiment.

Next, operation of the heating control system for the gas sensor of the engine will be explained, referring to a flowchart shown in FIG. 3. The flowchart in FIG. 3 shows control contents of energization to the heater 22 performed by the microcomputer 131. In the energization control, the ECU 13 measures an elapsed period since the engine is started until an ignition key is switched off, and stores the elapsed period as a post-start elapsed period in the backup RAM. Meanwhile, the ECU 13 measures another elapsed period since the energization to the heater 22 is started in activation energization control until the ignition key is switched off, and stores the latter elapsed period as a heater accumulative energization period in the backup RAM.

First, in Step S101, it is determined whether the engine has been started in Step S101. More specifically, it is determined whether the ignition key 14 is switched on (IGkey ON) in Step S101. If the result of the determination in Step S101 is "YES", it is determined whether water droplets are adhering to the exhaust pipe 12 in Step S102. More specifically, it is determined whether a determination flag xBEXWET is 1 in Step S102. The determination flag xBEXWET is used for determining whether the water droplets are adhering to the exhaust pipe 12. If the determination flag xBEXWET is 1, it is determined that the water droplets are adhering to the exhaust pipe 12. If the result of the determination in Step S102 is "YES", exhaust pipe preheat energization control (exhaust pipe preheat control) is performed, and then, activation energization control is performed in Step S104. Following steps from the activation energization control are similar to conventional processing steps. In the activation energization control, energization to the heater 22 at the duty ratio of 100 percent is performed to supply the power capable of heating the A/F sensor 151 to activation temperature. After that, the duty ratio is feedback-controlled to maintain the A/F sensor 151 at the activation temperature.

If the result of the determination in Step S102 is "NO", it is determined whether water droplets are adhering to an inner surface of the cavity 201 of the A/F sensor 151 in Step S103. More specifically, it is determined whether a determination flag xBAFWET is 1 in Step S103. The determination flag xBAFWET is used for determining whether the water droplets are adhering to the A/F sensor 151. If the determination flag xBAFWET is 1, it is determined that the water droplets are adhering to the A/F sensor 151. If the result of the determination in Step S103 is "YES", sensor preheat energization control (sensor preheat control) is performed in Step S105 before the activation energization control.

If the result of the determination in Step S103 is "NO", the preheat energization control is prohibited and the activation energization control is started immediately in Step S106.

Figure 4:
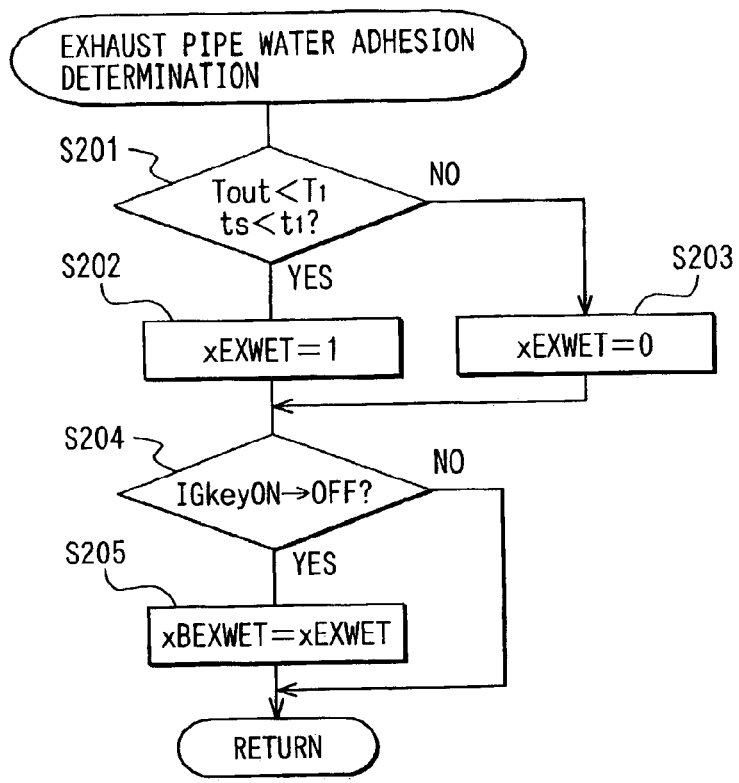
FIG. 4 is a second flowchart executed by the electronic control unit of the engine according to the first embodiment.

Next, estimation processing for determining whether the water is adhering to the exhaust pipe will be explained based on FIG. 4. First, in Step S201, it is determined whether ambient temperature $T_{out}$ detected by the ambient temperature sensor 16 is lower than a predetermined temperature $T_1$ and the post-start elapsed period $t_s$ is shorter than a predetermined period $t_1$. If the result of the determination in Step S201 is "YES", it is determined that the water droplets are adhering to the exhaust pipe, and a determination flag xEXWET is set to 1 in Step S202.

The determination is, firstly, based on the fact that the exhaust gas contains a large amount of water droplets immediately after the engine start because the entire engine is not heated to sufficiently high temperature, and if the engine stalls in such a condition, a large amount of water will exist in the exhaust pipe at the next engine start. More specifically, the determination is based on the following fact. That is, as the post-start elapsed period $t_s$ extends, the temperature of the entire engine including the exhaust pipe 12 increases gradually. Accordingly, the water droplets included in the exhaust gas are vaporized and reduced. On the other hand, if the post-start elapsed period $t_s$ is short, the entire engine including the exhaust pipe 12 has not been heated to the sufficiently high temperature yet. Accordingly, the water droplets included in the exhaust gas are likely to remain there.

Secondly, the determination is based on the following fact. That is, even if the post-start elapsed period $t_s$ is identical, the entire engine including the exhaust pipe 12 reaches the sufficiently high temperature when the ambient temperature $T_{out}$ is high. In such a case, saturation vapor pressure is high, and it can be estimated that water vaporization is promoted. On the other hand, when the ambient temperature $T_{out}$ is low, it can be estimated that the water vaporization does not proceed sufficiently even if the post-start elapsed period $t_s$ is identical.

If the result of the determination in Step S201 is "NO", it is determined that there is no water droplet adhering to the exhaust pipe 12, and the determination flag xEXWET is set to 0 in Step S203.

In Step S204 following Step S202 or Step S203, it is determined whether the ignition key 14 is switched off. The determination in Step S204 is determined negatively immediately after the ignition switch 14 is switched on. In this case, the processing proceeds to a return.

If the result of the determination in Step S204 is "YES", the flag xBEXWET is set to the value of the determination flag xEXWET at that time, and is stored in the backup RAM in Step S205. Then, the processing proceeds to the return.

Thus, the determination flag xBEXWET at the time when the ignition key 14 is switched off is learned. Under the condition that the ambient temperature $T_{out}$ is equal to or lower than the predetermined temperature $T_1$, the determination flag xEXWET remains 1 until the post-start elapsed period $t_s$ exceeds the predetermined period $t_1$ as a standard period, and the determination flag xEXWET becomes 0 if the post-start elapsed period $t_s$ exceeds the predetermined period $t_1$.

Thus, if the determination flag xEXWET is 1, it is determined that there is a high possibility that the water droplets are adhering to the inner surface of the exhaust pipe 12. Therefore, in the next engine start, the A/F sensor 151 is preheated with low heating energy, which causes no damage, until the water in the exhaust pipe 12 disappears before the activation energization control in Step S104. Thus, the damage to the A/F sensor 151 can be prevented.

Moreover, the A/F sensor 151 is heated already to some extent during the preheating by the time for starting the activation energization control. Therefore, the solid electrolyte layer 34 reaches the activation temperature quickly.

The time length "A" of the exhaust pipe preheat energization control interval shown in FIG. 3, or the waiting time to the activation energization control, is set based on the time when the water droplets in the exhaust pipe 12 are determined to be eliminated sufficiently by vaporizing the water droplets or delivering the water droplets downstream through the exhaust pipe 12. The time length "A" is determined through the experimentation and the like in advance in consideration of safety against the damage to the A/F sensor 151.

The predetermined temperature $T_1$ and the predetermined period $t_1$ are determined through the experimentation and the like in consideration of the safety against the damage to the A/F sensor 151.

Alternatively, the predetermined period $t_1$ for the post-start elapsed period $t_s$ may be extended or contracted in accordance with the ambient temperature $T_{out}$, and only a comparison between the post-start elapsed period $t_s$ and the predetermined period $t_1$ may be performed in the determination of Step S201.

Figure 5:
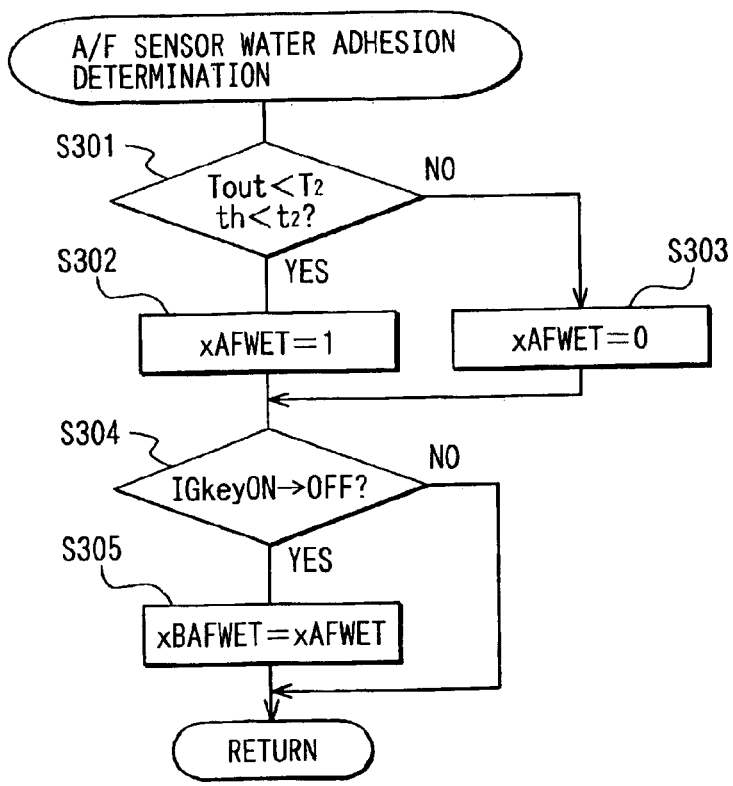
FIG. 5 is a third flowchart executed by the electronic control unit of the engine according to the first embodiment.

Next, estimation processing of the water adhesion to the A/F sensor 151 will be explained based on FIG. 5. First, in Step S301, it is determined whether the ambient temperature $T_{out}$ is lower than a predetermined temperature $T_2$ and a heater accumulative energization period (an accumulative energization period of the heater) $t_h$ is shorter than a predetermined period $t_2$. If the result of the determination in Step S301 is "YES", it is determined that the water is adhering to the A/F sensor 151, and a determination flag xAFWET is set to 1 in Step S302.

The determination is, firstly, based on the following fact. That is, the temperature of the A/F sensor 151 at the time when the engine is stopped is relatively high if the heater accumulative energization period $t_h$ is sufficiently long. Even if the water droplets adhere to the surface of the A/F sensor 151 and penetrate the trap layer 31 and the diffusion layer 32, and reach the cavity 201 after that, it can be estimated that the vaporization of the water sufficiently proceeds and that the water droplets are not contained in the cavity 201. On the other hand, if the heater accumulative energization period $t_h$ is short, there is a high possibility that the water droplets remain in the cavity 201 of the A/F sensor 151.

Secondly, the determination is based on the following fact. That is, even if the heater accumulative energization period $t_h$ is identical, it can be estimated that the water is vaporized when the ambient temperature $T_{out}$ is high. On the other hand, even if the heater accumulative energization period $t_h$ is identical, it can be estimated that the water remains in the form of droplets when the ambient temperature $T_{out}$ is low.

If the result of the determination in Step S301 is "NO", it is determined that there is no water droplet adhering to the A/F sensor 151, and the determination flag xAFWET is set to 0 in Step S303.

In Step S304 following Step S302 or Step S303, it is determined whether the ignition key 14 is switched off. The determination is determined negatively immediately after the ignition key 14 is switched on. In this case, the processing proceeds to the return.

If the result of the determination in Step S304 is "YES", the flag xBAFWET is set to the value of the determination flag xAFWET at that time, and is stored in the backup RAM in Step S305. Then, the processing proceeds to the return.

Thus, the determination flag xBAFWET at the time when the ignition key 14 is switched off is learned. Under the condition that the ambient temperature $T_{out}$ is equal to or lower than the predetermined temperature $T_2$, the determination flag xAFWET remains 1 until the heater accumulative energization period $t_h$ exceeds the predetermined period $t_2$, and the determination flag xAFWET becomes 0 when the heater accumulative energization period $t_h$ exceeds the predetermined period $t_2$.

Thus, if the determination flag xAFWET is 1, it is determined that there is a high possibility that the water is adhering to the inner surface of the cavity 201 of the A/F sensor 151. Accordingly, in the next engine start, the A/F sensor 151 is preheated with low heating energy, which causes no damage to the A/F sensor 151, before the activation energization control in order to eliminate the water droplets in the cavity 201 in Step S105. Thus, the damage to the A/F sensor 151 can be prevented.

The time length "B", of the sensor preheat energization control interval shown in FIG. 3 is set based on the time when the water in the cavity 201 is determined to be vaporized. The time length "B" is determined in advance through the experimentation and the like in consideration of safety against the damage to the A/F sensor 151. If the temperature of the A/F sensor 151 reaches 100° C., or the boiling point of the water, there is no need to continue the sensor preheat energization control further.

The predetermined temperature $T_2$ and the predetermined period $t_2$ should be preferably set in advance through the experimentation and the like in consideration of the required safety against the damage to the A/F sensor 151.

Alternatively, the predetermined period $t_2$ may be extended or contracted in accordance with the ambient temperature $T_{out}$, and only the comparison between the heater accumulative energization period $t_h$ and the predetermined period $t_2$ may be performed in the determination of Step S301.

(Second Embodiment)

Next, control of the energization to the heater 22 of the A/F sensor 151 performed by an ECU 13 according to the second embodiment will be explained based on a flowchart shown in FIG. 6.

The control performed by the ECU 13 according to the second embodiment is generally similar to that of the first embodiment. However, in the energization control according to the second embodiment, the duty ratio of the driving current applied to the heater 22 of the A/F sensor 151 is set in a method different from that of the control according to the first embodiment. The processing flow for setting the duty ratio is shown in the flowchart in FIG. 6. The processing shown in FIG. 6 is started when the engine is started, or when the ignition key 14 is switched on.

In Step S401, the ambient temperature $T_{out}$ is inputted. Then, in Step S402, it is determined whether the water is adhering to the exhaust pipe 12 based on the determination flag xBEXWET. If the result of the determination in Step S402 is "YES", heater duty map search ambient temperature $T_{outtemp}$ is set to $-30°$ C. in Step S404. Then, the processing proceeds to Step S407.

If the result of the determination in Step S402 is "NO", it is determined whether the water is adhering to the A/F sensor 151 based on the determination flag xBAFWET in Step S403. If the result of the determination in Step S403 is "YES", the heater duty map search ambient temperature $T_{outtemp}$ is set to $-10°$ C. in Step S405. Then, the processing proceeds to Step S407.

If the result of the determination in Step S403 is "NO", the processing proceeds to Step S406 and the heater duty map search ambient temperature $T_{outtemp}$ is set to the value of the ambient temperature $T_{out}$ inputted in Step S401. Then, the processing proceeds to Step S407.

In Step S407, a duty ratio corresponding to the heater duty map search ambient temperature $T_{outtemp}$ is read out from a heater duty map as the duty ratio in the heater energization period.

Figures 6, 7:
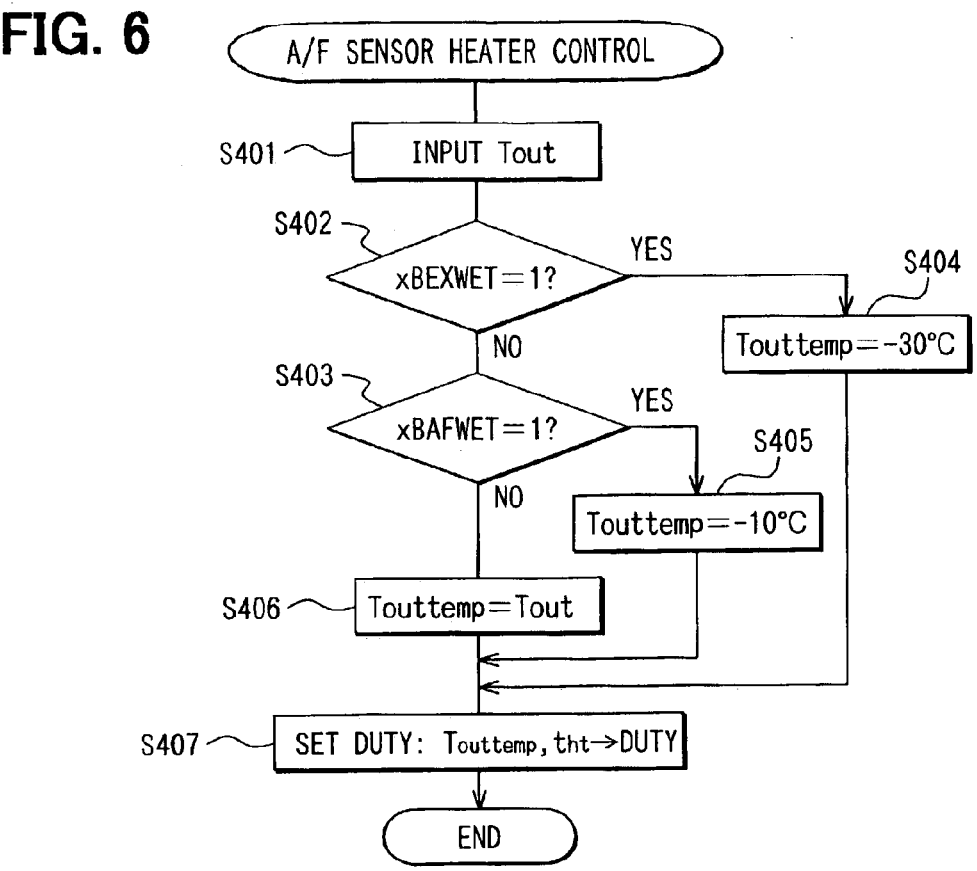
FIG. 6 is a flowchart executed by an electronic control unit of an internal combustion engine having a heating system for a gas sensor of the engine according to a second embodiment of the present invention.
FIG. 7 is a table showing contents of control performed by the electronic control unit according to the second embodiment.

As shown by the heater duty map in FIG. 7, a group of seven duty ratios corresponds to each search ambient temperature $T_{outtemp}$ and provides a profile of the energization current since the engine is started until the activation energization control is started. More specifically, after the ignition key 14 is switched on, the duty ratio set in the energization control is repeatedly renewed to each read duty ratio at predetermined timing $t_{ht}$ as shown in FIG. 7. The heater duty map is made so that the preheat energization control is performed if the search ambient temperature $T_{outtemp}$ becomes lower than 0° C. If the preheat energization control is performed, the duty ratio is set to be equal to or less than 30% for a long period before the duty ratio becomes 100%. The duty ratio is set to be equal to or less than 30% for a longer period as the search ambient temperature $T_{outtemp}$ decreases. The duty ratio in the preheat energization control is decreased as the search ambient temperature $T_{outtemp}$ decreases.

If there is a possibility of the water adhesion to the exhaust pipe 12, the search ambient temperature $T_{outtemp}$ is set to $-30°$ C. regardless of the actual ambient temperature $T_{out}$. Then, like the case of low temperature of $-30°$ C., the preheat energization control is performed for 100 seconds at a low duty ratio of 30%. This control is equivalent to the exhaust pipe preheat energization control. Thus, the heating performance can be reduced easily.

If there is a possibility of the water adhesion to the A/F sensor 151, the search ambient temperature $T_{outtemp}$ is set to $-10°$ C. regardless of the actual ambient temperature $T_{out}$. Then, like the case of low temperature of $-10°$ C., the preheat energization control is performed for 10 seconds at a low duty ratio of 30%. This control is equivalent to the sensor preheat energization control.

In the embodiment, also in the case where the actual ambient temperature $T_{out}$ is low, preheat energization control equivalent to the exhaust pipe preheat energization control or the sensor preheat energization control is performed regardless of the post-start elapsed period $t_s$ or the heater accumulative energization period $t_h$. This scheme focuses on the following fact. That is, if the ambient temperature $T_{out}$ is low, the saturated vapor pressure is low and there is a high possibility of the existence of the water droplets. Therefore, the ambient temperature $T_{out}$ can be employed as a parameter for determining whether the water is adhering to the exhaust pipe 12 or the A/F sensor 151. Thus, conditions used for determining whether the water is adhering to the exhaust pipe 12 or the A/F sensor 151 can be set appropriately.

In the second embodiment, the case of performing the exhaust pipe preheat energization control, the case of performing the sensor preheat energization control or the case of prohibiting the preheat energization control can be treated uniformly based on the single heater duty map. Therefore, the control constitution is simplified.

(Third Embodiment)

Figure 8:
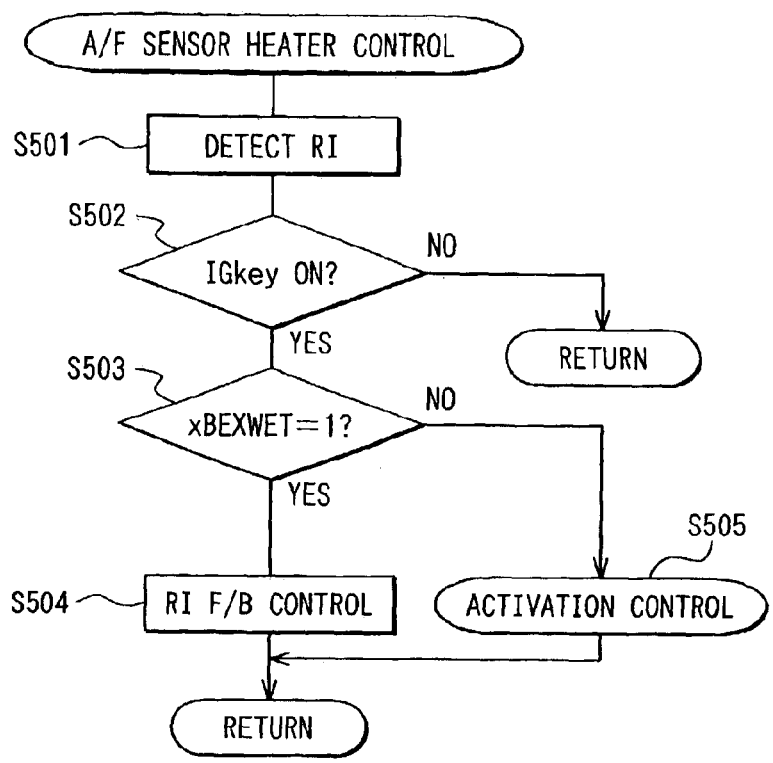
FIG. 8 is a flowchart executed by an electronic control unit of an internal combustion engine having a heating system for a gas sensor of the engine according to a third embodiment of the present invention.

Next, energization control of the heater 22 of the gas sensor 151 performed by an ECU 13 according to the third embodiment will be explained based on a flowchart shown in FIG. 8.

The control performed by the ECU 13 according to the third embodiment is generally similar to that of the first embodiment. However, in the energization control performed by the ECU 13 of the third embodiment, a duty ratio of the driving current applied to the heater 22 of the A/F sensor 151 is set in a method different from that of the first embodiment.

Figure 9:
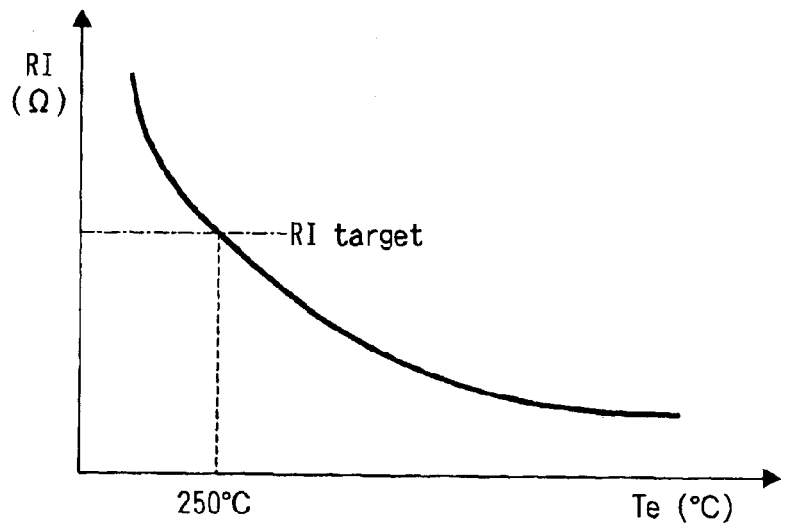
FIG. 9 is a graph showing contents of control performed by the electronic control unit according to the third embodiment.

First, in Step S501, resistance RI between the electrodes 38, 39 of the pump cell 21 of the A/F sensor 151, or element resistance RI, is detected. The element resistance RI correlates with temperature $T_e$ of the A/F sensor 151 as shown in FIG. 9. Therefore, the element resistance RI is employed as a parameter of the temperature $T_e$ of the A/F sensor 151. More specifically, a general method to calculate the element resistance RI from a gradient of the current with respect to the voltage in a non-limiting current area can be employed.

Then, in Step S502, it is determined whether the engine has been started. More specifically, it is determined whether the ignition key 14 is switched on (IG key ON) in Step S502. If the result of the determination in Step S502 is "YES", it is determined whether the water is adhering to the exhaust pipe 12 based on the determination flag xBEXWET in Step S503. If the result of the determination in Step S503 is "YES", element resistance feedback control (RI F/B control) is performed in Step S504. In the element resistance feedback control, the duty ratio is feedback-controlled so that the detected resistance RI provided in Step S501 converges to a predetermined target element resistance $RI_{target}$. As the element resistance feedback control, PID control can be employed. The element resistance feedback control is provided by equations (1) and (2), for instance. In the equations, D represents the duty ratio, and Kp and KI are gains.

$$\Delta RI = RI_{target} - RI \quad (1)$$

$$D = Kp \times \Delta RI + KI \times \int \Delta RI \quad (2)$$

After the element resistance feedback control is performed for a predetermined period, the activation energization control is performed with the duty ratio of 100%. Thus, the temperature $T_e$ of the A/F sensor 151 is increased to the activation temperature quickly.

By setting the target element resistance $RI_{target}$ to the resistance corresponding to the temperature at which the damage is not caused even if the water contacts the A/F sensor 151, the temperature $T_e$ of the A/F sensor 151 can be increased to the activation temperature quickly after the activation energization control is started, while preventing the damage. Inventors ascertained that the upper limit temperature $T_e$ for preventing the damage to the A/F sensor 151 is 300° C. Therefore, the target element resistance $RI_{target}$ is set to a value corresponding to temperature of 250° C., for instance.

If the result of the determination in Step S503 is "NO", the activation energization control is performed without performing the preheat energization control in Step S505.

In any cases, after the activation energization control is performed, control for maintaining the A/F sensor 151 at a predetermined temperature is performed.

In the third embodiment, the temperature of the A/F sensor 151 can be brought to the appropriate temperature regardless of the ambient temperature $T_{out}$ and the like. Therefore, the damage to the A/F sensor 151 can be prevented more suitably.

In the third embodiment, the water adhesion to the exhaust pipe 12 is determined. Alternatively, the water adhesion to the A/F sensor 151 may be determined. In this case, the target element resistance $RI_{target}$ is set to resistance corresponding to temperature around which the water gradually vaporizes in the cavity 201 of the A/F sensor 151 without bumping. For instance, the target element resistance $RI_{target}$ is set to a value corresponding to temperature of 100° C.

Alternatively, like the first embodiment, the existence of the water adhesion to the exhaust pipe 12 and to the A/F sensor 151 may be determined. Then, the target element resistance $RI_{target}$ may be changed based on the possibility of the existence of the water adhesion to the exhaust pipe 12 or the A/F sensor 151.

(Modifications)

In the first embodiment, the heater accumulative energization period $t_h$ is employed as the parameter representing the temperature of the A/F sensor 151. Alternatively, accumulative electric power applied to the heater 22 may be employed as the parameter representing the temperature of the A/F sensor 151. Alternatively, like the third embodiment, the temperature of the A/F sensor 151 may be estimated based on the element resistance and the like correlating with the temperature of the A/F sensor 151.

The water adhesion in the exhaust pipe 12 or the cavity 201 of the A/F sensor 151 may be determined based on parameters such as an intake flow rate, which provides exhaust gas quantity and quantity of generated water, exhaust temperature, which provides the saturated vapor pressure of the exhaust gas, or cooling water temperature, which represents the temperature of the entire engine including the exhaust pipe 12. In these cases, like the embodiments, the above parameters may be used for the determination in a combined fashion, or simply, may be used individually.

When it is determined that the water is adhering to the exhaust pipe 12, the activation energization control may be performed simply after a predetermined waiting period, without performing the exhaust pipe preheat energization control. Thus, delay in the activation energization control is limited to the case where there is a possibility of the water adhesion in the exhaust pipe 12. As a result, requirement for quick start of the A/F sensor 151 is met adequately.

In the embodiments, the exhaust pipe preheat energization control or the sensor preheat energization control is performed when it is determined that the water is adhering to the exhaust pipe. Alternatively, the exhaust pipe preheat energization control or the sensor preheat energization control may be performed invariably before the activation energization control, omitting the determination of the existence of the water adhesion in the exhaust pipe 12 or in the cavity 201 of the A/F sensor 151.

The present invention can be applied to an internal combustion engine having gas sensors for detecting gas concentration such as nitrogen oxides, carbon monoxide, hydrocarbon and the like, in addition to the A/F sensor.

The present invention should not be limited to the disclosed embodiments, but may be implemented in many other ways without departing from the spirit of the invention.

What is claimed is:

1. A heating control system for controlling energization to a heater of a gas sensor disposed in an exhaust pipe of an internal combustion engine, the heating control system comprising:

exhaust pipe water determining means for determining whether water droplets exist in the exhaust pipe when the engine is re-started, based on the preceding operation of the engine; and activation energization controlling means for performing activation energization control for energizing the gas sensor with electric power capable of heating the gas sensor to activation temperature after a predetermined waiting period passes following the engine re-start if the exhaust pipe water determining means determines affirmatively.

2. The heating control system as in claim 1, wherein the exhaust pipe water determining means determines affirmatively when an elapsed period from the preceding start to the last stop of the engine is shorter than a predetermined period.

3. The heating control system as in claim 1, further comprising:

preheat energization controlling means for performing preheat energization control for energizing the gas sensor with lower electric power than in the activation energization control before the activation energization control if the exhaust pipe water determining means determines affirmatively.

4. The heating control system as in claim 3, wherein the heating control system energizes the heater in duty cycle control and sets a smaller on-duty ratio in the preheat energization control than in the activation energization control.

5. The heating control system as in claim 3, wherein the preheat energization controlling means feedback-controls the energization to the heater so that the temperature of the gas sensor is brought to a predetermined temperature.

6. A heating control system for controlling energization to a heater of a gas sensor disposed in an exhaust pipe of an internal combustion engine, the gas heating control system comprising:

water determining means for determining whether a water amount in the exhaust pipe is larger than a predetermined amount when the engine is re-started, based on an operation state of the engine following a preceding engine start; and preheat energization controlling means for performing preheat energization control before activation energization control for energizing the gas sensor with electric power capable of heating the gas sensor to activation temperature, when the determining means determines that the water amount is larger than the predetermined amount, wherein the preheat energization controlling means energizes the gas sensor with lower electric power in the preheat energization control than in the activation energization control during a predetermined period in which there is a possibility that water droplets exist in the exhaust pipe.

7. The heating control system as in claim 6, wherein the water determining means determines that the water amount in the exhaust pipe is larger than the predetermined amount when an elapsed period from the preceding start to the last stop of the engine is shorter than a predetermined period.

8. A heating control system for controlling energization to a heater of a gas sensor disposed in an exhaust pipe of an internal combustion engine, the heating control system comprising:

water determining means for determining whether a water amount in the exhaust pipe is larger than a predetermined amount when the engine is restarted, based on an operation state of the engine following a preceding engine start; and preheat energization controlling means for performing preheat energization control before activation energization control for energizing the gas sensor with electric power capable of heating the gas sensor to activation temperature, when the determining means determines that the water amount is larger than the predetermined amount, wherein the preheat energization controlling means energizes the gas sensor with lower electric power in the preheat energization control than in the activation energization control so that water droplets in the gas sensor vaporize gradually and bumping of the water droplets is prevented.

9. The heating control system as in claim 8, wherein the water determining means that the water amount is larger than the predetermined amount when a temperature of the heater at the time when the engine was last stopped is lower than a predetermined temperature.

10. The heating control system as in claim 8, wherein the water determining means determines that the water amount in the exhaust pipe is larger than the predetermined amount when an elapsed period from the preceding start to the last stop of the engine is shorter than a predetermined period.

* * * * *